United States Patent [19]

Hunt et al.

[11] Patent Number: 4,949,172
[45] Date of Patent: Aug. 14, 1990

[54] DUAL-MODE TDI/RASTER-SCAN TELEVISION CAMERA SYSTEM

[75] Inventors: Robert P. Hunt, Palo Alto; David L. Gilblom, Los Altos, both of Calif.

[73] Assignee: Picker International, Inc., Highland Hts., Ohio

[21] Appl. No.: 293,960

[22] Filed: Jan. 6, 1989

Related U.S. Application Data

[63] Continuation-in-part of Ser. No. 249,385, Sep. 26, 1988, and a continuation-in-part of Ser. No. 186,446, Apr. 26, 1988.

[51] Int. Cl.[5] .............................................. H04N 7/18
[52] U.S. Cl. .................................. 358/101; 358/213.26
[58] Field of Search ................. 358/101, 106, 107, 93, 358/909, 213.13, 213.23, 213.25, 213.26, 213.29, 213.31; 382/8; 250/223 R, 562, 563, 572, 578; 356/237

[56] References Cited

U.S. PATENT DOCUMENTS

| Re. 32,164 | 5/1986 | Kruger | 378/19 |
|---|---|---|---|
| 4,366,574 | 12/1982 | Hill | 378/99 |
| 4,546,444 | 10/1985 | Bullis | 250/572 X |
| 4,578,810 | 3/1986 | MacFarlane et al. | 358/106 X |
| 4,663,669 | 5/1987 | Kinoshita et al. | 358/213.26 X |
| 4,689,686 | 8/1987 | Hashimoto et al. | 350/213.26 |
| 4,714,963 | 12/1987 | Vogel | 358/213.26 |
| 4,794,453 | 12/1988 | Gnuechtel et al. | 358/148 X |
| 4,811,106 | 3/1989 | Burt et al. | 358/213.26 |
| 4,811,409 | 3/1989 | Cavan | 358/101 X |
| 4,845,566 | 7/1989 | Sakai et al. | 358/213.31 |

Primary Examiner—Howard W. Britton
Assistant Examiner—Victor R. Kostak
Attorney, Agent, or Firm—Fay, Sharpe, Beall, Fagan, Minnich & McKee

[57] ABSTRACT

A mode selecting switch (74) selectively interconnects one of an external timing signal from a tachometer (32) and master timing signals from a raster-scan synchronization generator (70) with a sensor line shift timing generator (76). In a time delay and integration mode, the sensor line shift timing generator causes the CCD arrays of an image section (22) and storage section (24) to shift pixel values down the CCD arrays at a rate commensurate with the external timing signal. As a spot of light emanating from a portion of an object moving through an examination region moves along the CCD array, a corresponding pixel charge is shifted through the CCD array at the same speed such that the same pixel charge integrates light from the same spot as it moves the entire length of the CCD array. In a raster-scan mode, the mode selecting switch connects master timing signals from the raster scan sync generator to the sensor line shift timing generator which generates conventional raster-scan timing signals. An output register timing generator (78) generates timing signals under control of an oscillator (80) for output registers (26) such that an output signal is produced that is compatible with EIA-170 television signal standard. Video processing channels (50) and a video synchronization circuit (60) process the output signals to produce a composite video signal.

21 Claims, 4 Drawing Sheets

DUAL-MODE TDI/RASTER-SCAN TELEVISION CAMERA SYSTEM

This application is a continuation-in-part of U.S. Patent applications Ser. No. 249,385, filed Sept. 26, 1988 and Ser. No. 186,446, filed Apr. 26, 1988.

BACKGROUND OF THE INVENTION

The present invention relates to the video camera art. It finds particular application in conjunction with quality control and monitoring with video cameras, especially of continuous material processes, and will be described with particular reference thereto. It is to be appreciated that the invention may find other applications including document recording, photographic film scanning, photographic archival recording, object tracking, video security, and the like.

Heretofore, quality control and monitoring has been carried out with charge coupled devices (CCD) and other video cameras. In one method, a video output signal was generated which included a long, continuous series of video image fields. In a frame transfer CCD camera, light from a continuous or pulsed source was focused on an image section of a CCD sensor for a selected interval of time. The interval was selected to produce good image contrast without significant blurring of the image due to object motion. The charge on each element of the image section was indicative of received light intensity. The charge was transferred during a vertical blanking interval, e.g. a few hundred microseconds, into corresponding elements of an optically insensitive CCD mass storage section. As the image section again commenced integrating received light, the charge was read out element by element from the optically insensitive elements to form a video signal representing one field of the resultant image. After the 1/60th of a second or other selected read out interval, the charge representing the second field was transferred from the image section to the storage section. As the second field was read out of the storage section, the second video signal image section started integrating light to form a third field. This sequence was repeated cyclically to form a video signal representing a series of single image fields.

Continuous production of image fields rendered CCD cameras awkward to adapt for certain high volume quality control situations. As a continuous sheet or individual object was moved past the CCD camera, the resultant video signal represented a long series of image fields. In order to review the images of each object to monitor for a controlled characteristic, it was first necessary to determine which portion of the video signal included the field(s) which represented the monitored individual object or portion of the continuous sheet. Second, it was necessary to determine within the field the actual location of the monitored object or sheet portion. When increased lighting was necessary, the actuation of a strobe light was coordinated with the field of interest. If the strobe light was not completely coincident with a common location of the object or sheet portion within the field(s) of interest, lighting intensities and object shapes would vary among the fields of interest for each object or sheet portion. If the stream of objects or sheet was moving rapidly compared with 1/60th of a second or other one field exposure time, then each object would be in a different position within the selected field of interest. This different positioning of the object not only required identifying the object position in the video field, but could also result in different lighting conditions on the object. These inaccuracies in the timing, positioning, and lighting of the monitored objects all limited the degree of accuracy and the speed with which quality control monitoring could be performed.

In the quality control and monitoring method described in parent patent application Ser. No. 186,446, filed Apr. 28, 1988, a CCD device is asynchronously triggered at a controlled instant in time to "grab" a moving object. The instant in time is synchronized with the moving object's entry to a preselected examination point. A high intensity strobe is flashed concurrently with asynchronously triggering a CCD device to "grab" the moving object. While such a method has certain unique advantages, it requires a significant amount of power capacity to flash the high intensity light necessary for its functioning. The minimum cycle time of the strobe limited the speed of the conveying system.

Although asynchronous triggering is applicable to continuous web monitoring, some webs are advanced at such high speeds that the repower time of the strobe may limit the web advancement speed. Additionally, inspection of continuous webs with cameras producing a series of individual fields requires matching the tops and bottoms of adjacent fields to provide a single complete image of the web without gaps or overlaps. Processes in which continuous webs are advanced include the fabrication of sheets and films of plastics such as polyethylene, MYLAR, cellophane and vinyl, metals, glass, plywood, paper and other wood pulp products, fabrics, printing of newspapers, magazines, wallpaper, packaging, etc., lamination of plastics, composites, paper, etc., coating of plastics, metals, etc. with paint, magnetic particles, abrasives, adhesives, photographic emulsions, electrically conductive materials, etc., and embossing, cutting, slitting, perforating, etc. of any of the aforementioned raw or processed materials.

In the past, some of these webs have been imaged using line-scan cameras, that is, cameras using sensors constructed of a single row of photosensitive areas. The range of application of such sensors has been severely limited due to the low maximum speed at which the web can travel and due to the large amount of illumination necessary to produce usable signals from the sensor. In addition, because line-scan sensors cannot produce images when the web motion is stopped, focusing and alignment of such systems is difficult.

Cameras using the time-delay-and-integration (TDI) scanning mode have been built in the past for military aerial reconnaissance and some other specialized applications. However, these have not been usable in web inspection because they could not be synchronized with the web motion. Their utility was further limited because they could not acquire images unless the object being viewed was moving at the correct velocity relative to the camera. This makes system set-up with static objects nearly impossible.

The present invention contemplates a new and improved video camera system and method which overcomes the above referenced problems and others.

SUMMARY OF THE INVENTION

In accordance with the present invention, a dual mode CCD camera is provided. A switching means selectively switches one of external timing signals and master timing signals from an internal synch generator to a timing generating means. The timing generating means produces clock signals for controlling shifting of charge values along a CCD array. A lens focuses light from a region of interest on at least a portion of the CCD array.

In accordance with a more limited aspect of the present invention, the dual mode CCD camera includes a CCD image section and a storage section. A serializing means serializes pixel values from the storage section into an output video signal. A line shift timing generating means generates clocking signals for controlling the shifting of lines of pixel values through the image and storage sections. An output register timing generating means generates output register timing signals for clocking the pixel values from the serializing means. A reference oscillator is connected with the output register timing generating means for controlling the output register timing signals. A raster scan synch generating means produces master timing signals for a raster scan mode. A timing signal conditioning means conditions an externally generated timing signal for compatibility with the sensor line shift timing generating means. A switching means selectively switches one of the signal conditioning means and the raster scan synch generating means into electrical communication with the line shift timing generating means for connecting one of the master clock signals and conditioned external timing signals thereto.

In accordance with another aspect of the present invention, a CCD camera system is provided. A conveying means conveys at least one item through an examination region. A tachometer generates timing signals that vary in accordance with the speed of the conveying means through the examination region. A lens focuses light from the examination region on at least a portion of the CCD array. A timing generating means controls shifting of charge values along the CCD array, the timing means is connected with the tachometer in such a manner that it controls the transferring of pixel charge values along the CCD array in accordance with the conveying means speed dependent timing signal.

A first advantage of the present invention is that it performs scans in either a raster mode with static objects or TDI mode synchronized with object motion and that either mode may be selected at any time.

Another advantage of the invention is that it allows the rate at which the images are acquired to be controlled directly by the process producing the material to be viewed.

Another advantage of the present invention is that it consume less electrical power than cameras which require high intensity flashes to illuminate the object.

Another advantage of the present invention is that it permits monitoring under lower levels of lighting and nonflashed lighting.

Another advantage of the present invention is that it allows for monitoring of a continuous web process without overlapping. Identifying and recognizing the overlap between frames is eliminated.

Another advantage of the present invention is that it permits the routines used to process the video data when the camera is operating in the TDI mode in a system to be developed in the lab with static objects using the same camera thus avoiding discrepancies in the data quality which may occur if different cameras must be used in these two situations.

Yet another advantage of the present invention is that it refreshes pixel light values representing light received by light sensors, throughout the integration period.

Still further advantages of the present invention will become apparent to those of ordinary skill in the art upon reading and understanding of the following detailed description.

BRIEF DESCRIPTION OF THE DRAWINGS

The present invention may take form in various components and arrangements of components or in various steps and arrangements of steps. The figures are only for purposes of illustrating a preferred embodiment and are not to be construed as limiting the invention.

FIG. is a diagrammatic illustration of a TDI camera and quality control system in accordance with the present invention; and, FIG. 2A, 2B, and 2C taken together are a more detailed illustration of the system of FIG. 1.

DETAILED DESCRIPTION OF THE PREFERRED EMBODIMENT

Figure 1:
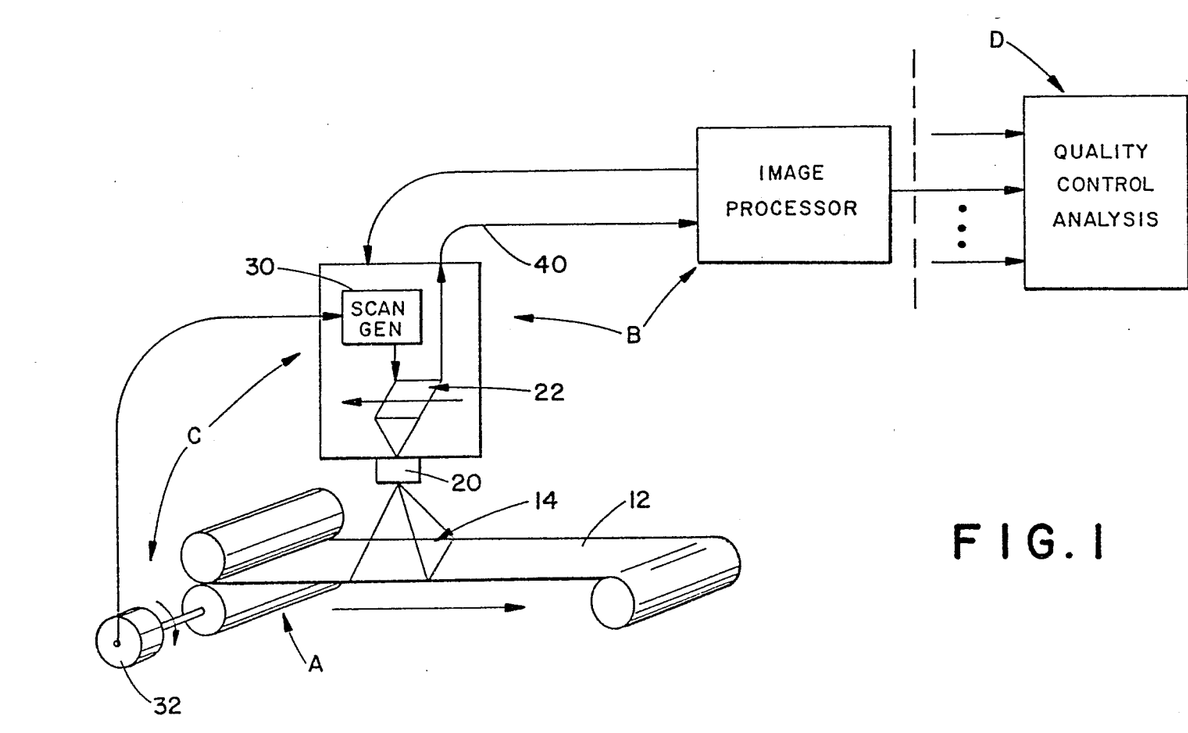

With reference to FIG. 1, conveying means A moves a continuous web, a line object, or the like to be examined through an examination region at an adjustable or irregular speed. A CCD camera or opto-electrical transducer system B monitors the moving object by focusing an image of the moving object(s) on an opto-electric transducer. As the object moves, the image moves correspondingly along the transducer. A synchronizing control means C synchronizes and coordinates movement of the object and conversion of the image into an electronic video signal by the camera B. Specifically, the transducer samples the same element or pixel of an image several times. The synchronizing means causes the multiple samplings corresponding to the same pixel of the image but sampled at different sampling times and different regions of the transducer to be integrated. The synchronizing means preferably adapts the sampling of the transducer to movement of the object. However, in some applications it is advantageous to vary the speed of the object to match the sampling of the transducer. A quality control analysis means D analyses the video signal for flaws, defects, or other characteristics of the web and denotes their locations.

Figure 2A:
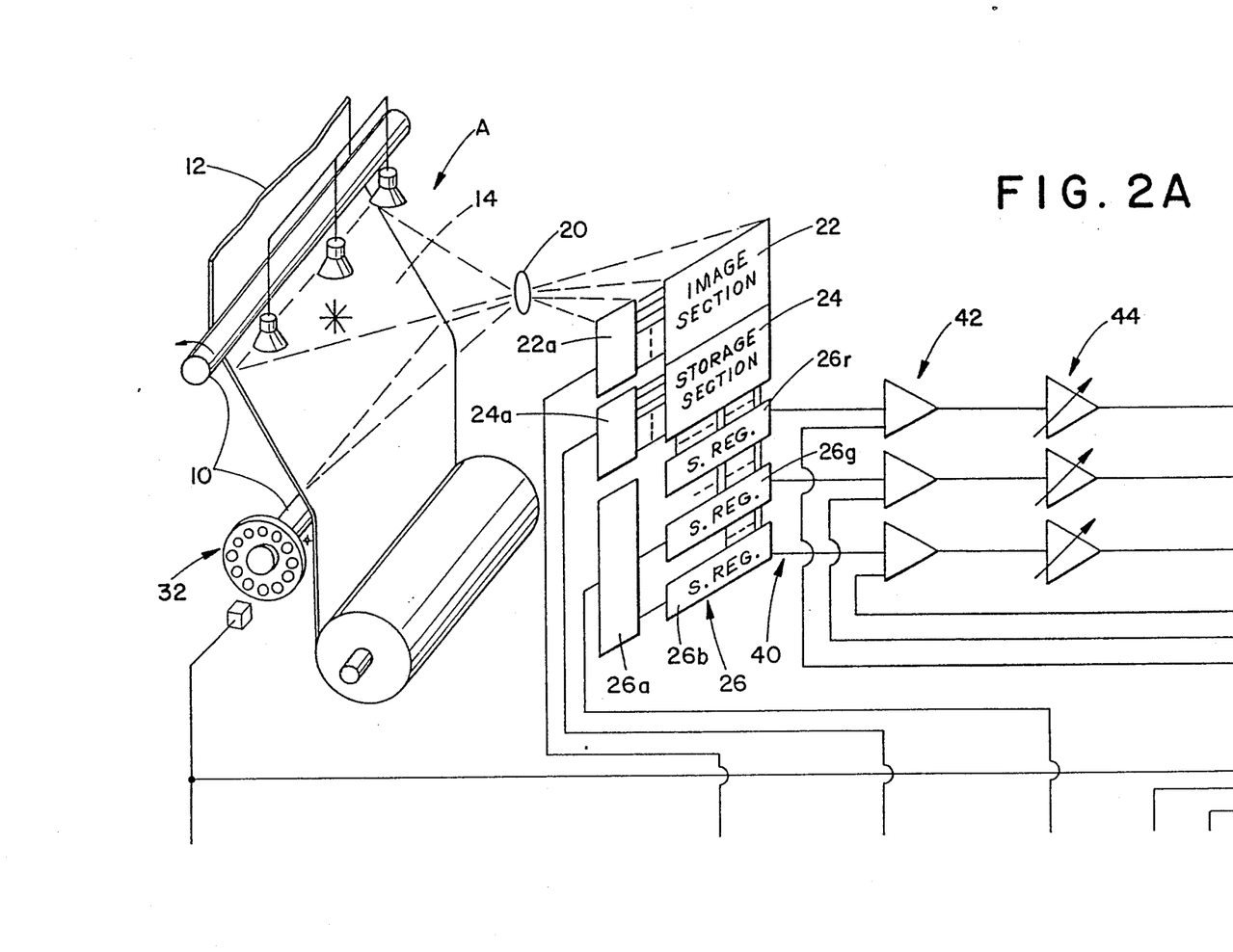

With continuing reference to FIGURE and further reference to FIG. 2A, the conveying means A includes a conventional conveyor 10 for a moving object 12 through the examination region 14. The nature of the conveyor is dependent on the object to be transported, as is known in the art. In the preferred embodiments, the conveyor includes rollers for a continuous web of floor coverings, wall paper, or other finished sheet goods. The examined subject may include sheets and films of plastics such as polyethylene, MYLAR, cellophane and vinyl, metals, glass, plywood, paper and other wood pulp products, fabrics, printing of newspapers, magazines, wallpaper, packaging, etc., lamination of plastics, composites, paper, etc., coating of plastics, metals, etc. with paint, magnetic particles, abrasives, adhesives, photographic emulsions, electrically conductive materials, etc., and embossing, cutting, slitting, perforating, etc. of any of the aforementioned raw or processed materials. Optionally, the conveyor may have pockets, recesses, or clamps for fixing the position of each received objects on the belt.

The camera B includes an optical system, such as a lens 20, which focuses light received from the examination region on a light sensitive area 22, preferably a bidirectional array of CCD elements. The lens focuses light emanating from the examination region continuously onto the light sensitive area or image section of the optoelectrical transducer. The resolution of the resultant image is determined by the number of CCD elements in each dimension. The more elements, the finer the resolution. A typical video camera might have a 244 x 610 element array. For color, a third of the elements have a green filter, a third have a blue filter, and a third have a red filter, or any other three color filter combination as is conventional in the art.

In conventional frame transfer CCD cameras, the data is periodically shifted from the image section 22 to a light shielded storage section 24 during a vertical flyback period which erases or resets each element of the CCD image section. In the TDI mode, the vertical flyback signals are defeated. The image section and storage section transfer are both connected to the synchronizing means C which step lines of pixels continuously at a line frequency rate to output registers 26. The synchronizing means controls the lines or rows of the photosensors 22, 24 in such a way that the accumulated charge is moved in synchronization with the light pattern arriving from the object being viewed. For example, when the web has a spot or blemish which passes through the examination region, the image of the spot is progressively transferred or shifted along the light sensitive area into the storage section 24. That is, as the object moves some small increment, the charge is shifted one row to follow the motion. If there are 100 rows of photoelements, then the total exposure time for each small area in the image will last 100 times as long as in a single-row imager. This permits the rows to be moved 100 times faster or for the intensity of the illumination to be reduced by 100. Interline-transfer CCD imagers as well as frame-transfer CCD imagers can also be used but require more complex support circuitry.

The charge values are shifted from row to row along the CCD array in precise synchronization with movement of the object being imaged and its image on the CCD array. For example, if the lens 20 focuses a 1 millimeter x millimeter area of the object on each element of the CCD array, then each time the object moves 1 millimeter, the pixel charge or integrated light value is shifted one row or line in the CCD array. In this manner, subsequent images on the CCD array superimpose directly on shifted previous images. By the time an image value or line of image values reaches the optically insensitive storage section 24 of the sensor, the optic information from the object has been integrated over the entire transfer period (1/10 second, for example). With the 244×610 CCD array, each pixel value represents the sum of light received at each of 244 CCD elements. The synchronization means C keeps monitored object movement and the image sensor transfer process in precise synchronization. In the preferred embodiment, the speed of the conveyor rollers, drive motors, or the like is converted by the synchronization means into clocking signals for the CCD array. Alternatively, signals from clocking electronics in the camera may be readjusted with variations in the speed of the conveyor.

In the time delayed integration mode, the pixel values in only the first line of the CCD array are refreshed each time. These pixel values are shifted along both the image and storage sections at a selectable speed and received light at each position is integrated. This is as opposed to the rapid transfer of pixel values from the image region to the storage region once per field in a frame transfer operation.

With continued reference to FIG. 2A, a signal conditioner 30 receives a trigger signal $t_i$ from a conveyor speed sensor or tachometer 32 and produces clock pulses to clock the CCD array at a corresponding rate. More specifically, the trigger signals control the frequency of an image section transfer clock or means 34, which supplies the clock signals to a light image sensor section control means 22a and a storage section control means 24a. The light image sensor control means 22a causes the charge of each image element or row of elements of the image section 22 to be shifted line by line. After just about 244 pulses or shift commands in the illustrated 244 active line image section embodiment, a line of charge values has been shifted 244 lines from the first line of the image section into the storage section 24.

The clocking signals are selected such that the image transfer is synchronized with the movement of the conveyor. The controller C conveys identical transfer clock pulses to the storage section control means 24a as sent to the image section control means 22a to cause the data from the storage section 24 to be shifted line by line into the shift registers means 26. To enable the camera to operate in either a conventional field mode or the time delay and integration mode, the storage section is the same size as the image section.

When using a color video image section, a red shift register 26r, a blue shift register 26b, and a green shift register 26g are provided. Alternatively, a color filter-free or black and white image section may be provided and a single black and white output shift register. Once a line of pixel or integrated light values have been transferred from the storage section 24 to the shift registers, the clocking means 34 sends higher speed three phase shift register clock signals to a shift register controller 26a. The shift registers serially step each charge or data value onto video signal output lines 40 before the next line is loaded into the shift registers from the storage section. Thus, between image or storage section transfer clock pulses, a number of shift register clock pulses equal to the number of elements per line are generated to clock out red, green, and blue (or black and white) output signals at a frequency and format that is compatible with EIA-170 television signal standards.

Feedback amplifiers 42 combine each of the three color output signals with a feedback signal which establishes a DC reference level to minimize the interfering effects of clock noise. A gain adjusting amplifier means 44 adjusts the gain of all three signal components correspondingly.

Figure 2B:
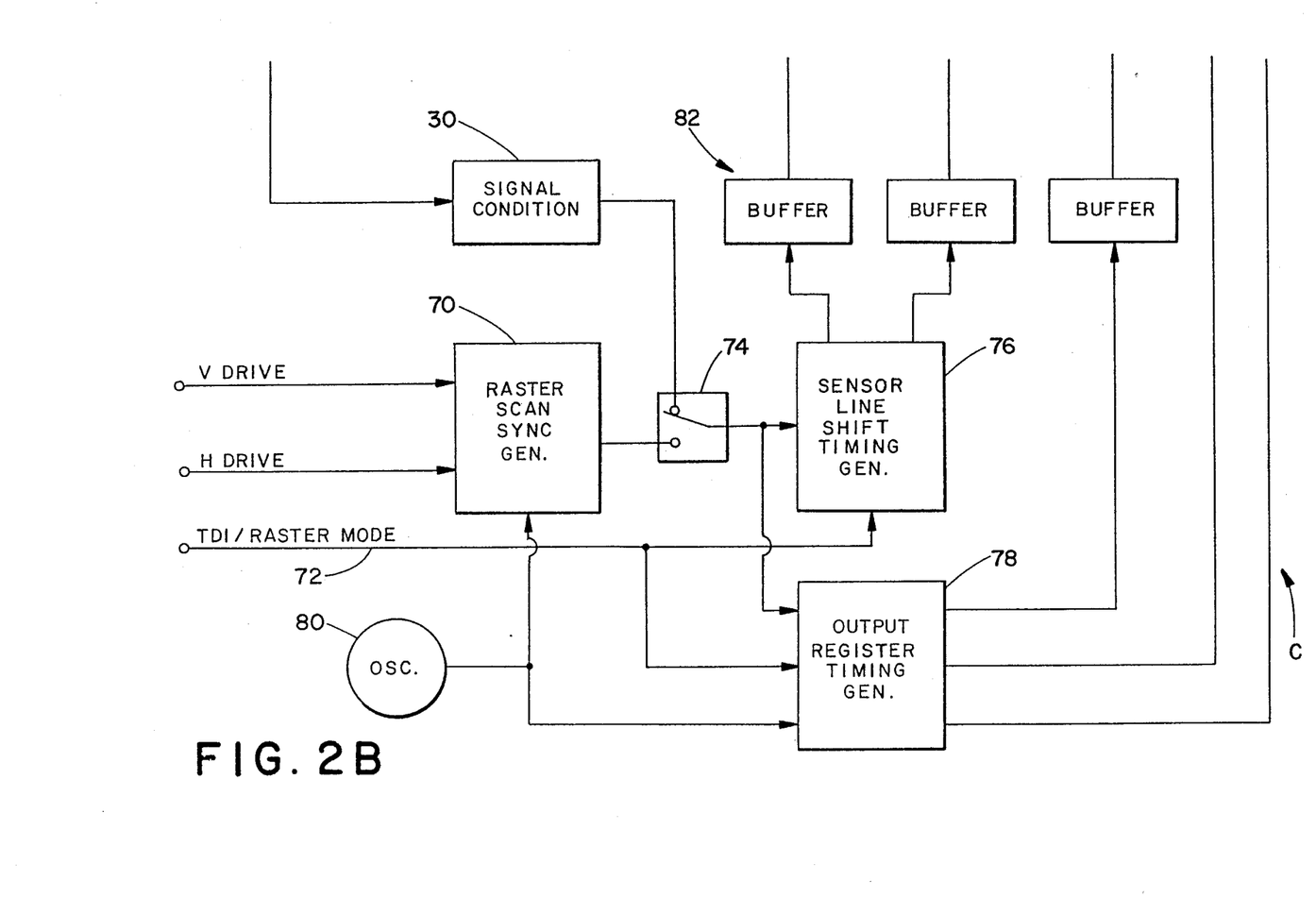
Figure 2C:
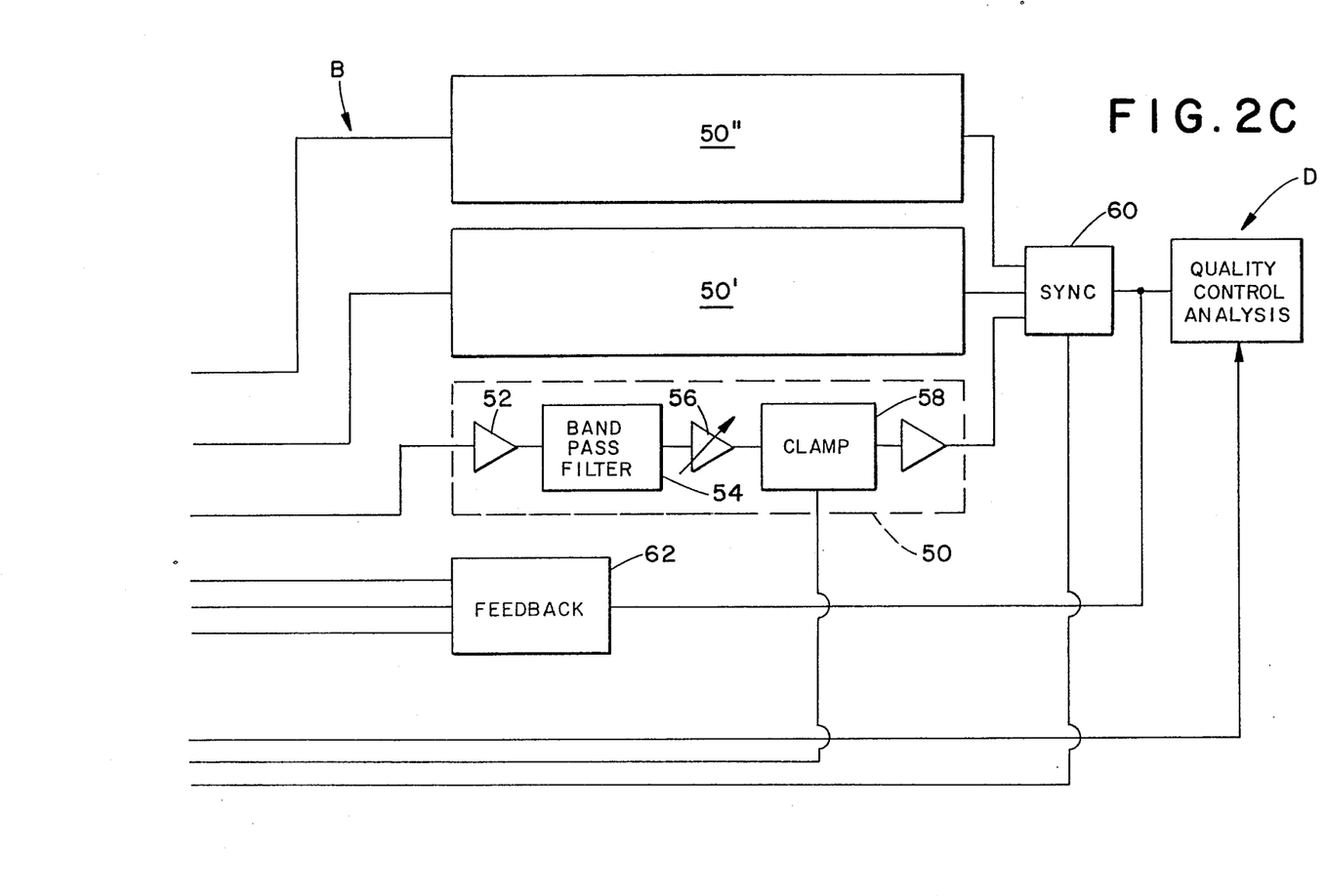

With reference to FIG. 2C, each color signal is processed by a light video channel 50, 50', and 50''. The video channel includes an impedance adjusting amplifier 52 for providing a low impedance output signal. A band pass filter 54 removes any vestiges of clocking signal noise or the like. A user controlled gain amplifier 56 amplifies the signal from the band pass filter and passes it to a clamping means 58 which restores the DC video. At the end of each horizontal sweep line, the clamping means shorts to a DC reference level to restore a DC level that sets the black level of the resultant image. A synchronization information means 60 switches between lines to reference voltages to add blanking and horizontal synchronization information to the signal. By convention, the synchronization means 60 only adds synchronization information to one, generally the green, video component. A feedback circuit 62 feeds back a portion of the composite video signal to provide a phase sensitive detection of the clocking to establish the DC level that minimizes the clock noise.

Preferably, the feedback signal also is based on a single one of the components. The video processing circuitry is stable to better than one part in 256 to enable precision digitizing and digital signal processing of the resultant video signal.

The quality control analysis means D receives the composite video signal and operates on it in a manner that is appropriate to the quality control function undertaken. For example, the analysis means D may turn the composite signal into a man-readable video image. Alternately, the analysis means may examine components of the video signal corresponding to selected regions to determine whether they meet preselected characteristics relative to each other, preselected standards, or the like.

Looking by way of example to monitoring a continuous web of solid color material, the image of the web may change in gray scale or color relative to the rest of the web image. The change may be the result of color changes in the web or surface deformates that alter the amount of reflected light. The pixel values of the video signal of the web are compared with a preselected gray scale characteristic or value to determine if the web is deformed or damaged beyond selected tolerances. If the web has a repeating pattern, the image or video signal is compared with corresponding standards which change cyclically with the pattern to determine whether the web has been accurately processed. If the web is monitored in color, each image or pixel value of the video signal is compared with one of a plurality of colorimetric standards in accordance with a location within the pattern. Alternately, color or other physical parameters may be used to sort various types or grades of products. Numerous other sorting, quality control, and acceptance algorithms may be implemented as are appropriate to the requirements of the objects being examined.

With reference to FIG. 2B, the synchronizing means C includes an internal raster scan sync generator means 70 which produces master timing signals for a raster-scan mode. The scan generator means may have either an internal crystal oscillator or external drive signals as its time base. A control line 72 receives input signals which enable the camera to operate in either the time delayed and integration (TDI) mode or the rasterscan mode. The mode selection signals control a switch 74 which connects the output of either the raster-scan generator 70 or the process speed controlled clock signal from the signal conditioner to a sensor line shift timing generator 76 and an output register timing generator 78. A crystal oscillator 80 controls the timing of the output register timing generator and provides camera timing in the raster-scan mode. In this manner, the clocking of the shift register 26, hence, the video signal, is independent of process speed. The sensor line shift generating means 76 converts the received timing signals of the selected mode into four-phase clocks for the image and storage sections. The output register timing generating means 78 provides three phase clocks for reading out the pixel charges from the output register. The output register timing generating means also sends clamp timing signals to the clamping means 58 of the video channels and to the synchronization means 60. Buffers 82 condition the three and four phase clock pulses for use by the sensor and shift register controls. The three phase clock signals for the output shift registers 26 are controlled by the oscillator 80 in both modes.

The preferred embodiment can be operated either in the above described time delay integration mode or as a conventional video camera. When the time delayed integration mode is selected, an approximate input on the vertical driver input 72 causes a mode select means 74 to cause the sensor line timing generator 76 to send the four-phase TDI clock sequences to the image and storage section control means 22a, 24a. When the conventional frame mode is selected, the raster-scan sync generator 70 causes the sensor line generator to send conventional four-phase frame transfer clock signals or interline transfer clock signals.

Although only a single camera is illustrated for simplicity in the preferred embodiment, it is to be appreciated that multiple cameras may be used. For example, the camera may view adjoining sections across the web. Alternately, two cameras may view sections along the direction of movement, with the cameras coordinated to alternate lines. The multiple cameras are operated in their raster scan mode on a stationary web to align the viewed sections.

In yet another application, the camera may be cycled between the raster and TDI modes to transfer different types of data. For example, the camera may alternately send images of people in the raster mode and documents in the TDI mode. This would permit the camera to function as a video phone and provide high resolution images or print outs of discussed documents or data.

The invention has been described with reference to the preferred embodiment. Obviously, modifications and alterations will occur to others upon reading and understanding the preceding detailed description. For example, as previously stated signals from the clocking controller electronics may be used to control the speed of the conveyor system. It is intended that the invention be construed as including all such alterations and modifications insofar as they come within the scope of the appended claims or the equivalents thereof.

Having thus described the preferred embodiment, the invention is now claimed to be:

1. A dual mode CCD camera comprising:

a CCD image section having an array of light sensitive elements for accumulating pixel values indicative of an accumulative amount of light received;

a storage section having an array of pixel storage elements, the storage section being electrically connected with the image section such that the pixel values are transferred from the image section to the storage section;

a serializing means for serializing the pixel values from the storage section into an output video signal;

a sensor line shift timing generating means for generating clocking signals for controlling the shifting of lines of pixel values through the image section and the storage section;

an output register timing generating means for generating output register timing signals for clocking the pixel values from the serializing means;

a reference oscillator operatively connected with the output register timing generating means for controlling the output register timing signals in accordance therewith;

a raster-scan sync generating means for producing master timing signals for a raster-scan mode;

a timing signal conditioning means for conditioning an externally generated timing signal for compatibility with the sensor line shift timing generating means; and, a switching means for selectively switching one of the signal conditioning means and the raster scan sync generating means into electrical communication with at least the sensor line shift timing generating means for providing master timing signals thereto such that the sensor line shift clock signals are coordinated with a selected one of the external timing signals and the raster-scan master timing signals.

2. A dual mode CCD camera comprising:

a CCD array having a plurality of lines of light sensitive elements for accumulating lines of pixel values each indicative of an accumulated amount of light received;

a lens means for focusing light from a region of interest on the CCD array;

a serializing means for serializing each line of pixel values from the CCD array into an output video signal;

a line shift means for shifting the lines of pixel values along the CCD array to the serializing means at a rate controlled by receiving timing signals;

a raster-scan sync generating means for generating master timing signals of a preselected frequency for a raster-scan mode;

a timing signal conditioning means for conditioning an externally generated timing signal of variable frequency for compatibility with the line shift timing means; and, a switching means for selectively switching one of the signal conditioning means and the raster scan sync generating means into electrical communication with the line shift means for providing timing signals thereto such that the lines of pixel data are shifted along the CCD array at a rate in accordance with the frequency of the timing signal from the selected one of the raster scan sync generating means and the timing signal conditioning means.

3. The camera as set forth in claim 2 further including a means for generating the external timing signals in accordance with movement of a means for moving a subject through the region of interest.

4. The camera as set forth in claim 3 wherein the lens means includes a shutterless leans for continuously focusing light from the region of interest adjacent the conveying means on the CCD array.

5. The camera as set forth in claim 4 further including an illuminating means for continuously illuminating the region of interest.

6. The camera as set forth in claim 2 further including:

an amplifier means operatively connected with the serializing means;

a band pass filter for removing clocking signal noise, the band pass filter being operatively connected with the amplifier means;

a clamping means for restoring DC video, the clamping means being operatively connected with the band pass filter; and, a synchronizing means for adding blanking and horizontal synchronization information to the output video signal to produce a composite video signal.

7. The camera as set forth in claim 6 further including a feedback circuit for feeding back a portion of the composite video signal to a feedback amplifier means, the feedback amplifier means being operatively connected with the serializing means for combining the output video signal and the fedback composite video signal portion.

8. A CCD camera comprising:

a switching means for switching one of external timing signals and master timing signals from an internal sync generator to a timing generating means, the timing generating means producing clock signals for controlling shifting of lines of charge values along a CCD array means, and, a lens for focusing light from a region of interest on at least a portion of the CCD array means.

9. The camera as set forth in claim 8 further including a shift register means for serializing charge values received from the CCD array means to produce an output video signal.

10. The camera as set forth in claim 9 further including at least one video processing channel for converting the output video signal into a composite video signal.

11. The camera as set forth in claim 9 further including an output register timing means for generating timing signals for the shift register means.

12. The camera as set forth in claim 11 further including an internal oscillator operatively connected with the output register timing generator means for providing timing signals to control the operation thereof.

13. The camera as set forth in claim 12 further including a means for producing external timing signals at a frequency that varies in accordance with a conveying means which conveys at least one object through the region of interest, the external timing signal producing means being operatively connected with he switching means such that the switching means connects one of external timing signals from the external timing signal producing means and master timing signals from the internal sync generator with the timing generating means.

14. A CCD camera system comprising:

a conveying means for conveying at least one item to be examined through an examination region;

a conveying means speed dependent timing signal means for generating conveying means speed dependent timing signals that vary in accordance switch a speed of the conveying means through the examination region;

a lens which focuses light from the examination region on at least a portion of a CCD array; and, a timing generator means for controlling shifting of charge values along the CCD array, the timing means being operatively connected with the conveying means speed dependent timing signal means such that the timing generator means controls the transferring of pixel charge values along the CCDE array in accordance with the conveying means speed dependent timing signal.

15. The camera system as set forth in claim 14 wherein the lens focuses light from a portion of an object moving through the examination region onto a progression of pixels of the CCD array and wherein the timing generating means shifts pixel charges along the CCD array such that a pixel charge corresponding to the examined object portion is shifted along the CCD array at the same rate that the focused light from the object portion moves along the CCD array.

16. The camera system as set forth in claim 14 further including an internal synchronization generator means for generating master timing signals for a raster-scan mode and a mode selecting means for selectively connecting one of the conveying means speed dependent timing signals and master timing signals from the internal synchronization generator with the timing generator means such that the camera system is selectively operable in one of a time delayed and integration mode and raster-scan mode.

17. The camera system as set forth in claim 16 further including a shift register means for serializing charge values received from the CCD array means to produce an output signal.

18. The camera system as set forth in claim 19 further including an output register timing means for generating timing signals for the output register means.

19. The camera system as set forth in claim 14 further including a lighting means for lighting the examination region with continuous illumination.

20. The camera system as set forth in claim 19 wherein the conveying means includes means for conveying a continuous web through the examination region.

21. The camera system as set forth in claim 20 further including an analysis means for comparing signals from the CCD arrays with preselected standards to determine whether the continuous web is in conformity therewith.

* * * * *

UNITED STATES PATENT AND TRADEMARK OFFICE
CERTIFICATE OF CORRECTION

PATENT NO. : 4,949,172

DATED : August 14, 1990

INVENTOR(S) : Robert P. Hunt and David L. Gilblom

It is certified that error appears in the above-identified patent and that said Letters Patent is hereby corrected as shown below:

In column 4, line 15, please change "FIG." to --FIG. 1--; and,

In column 4, line 46, please change "FIGURE" to --FIGURE 1--.

<u>In the Claims:</u>

In column 9, line 48, please change "leans" to --lens--;

In column 10, line 34, please change "he" to --the--;

In column 10, line 46, please change "switch" to --with--; and,

In column 10, line 56, please change "CCDE" to --CCD--.

Signed and Sealed this

Twenty-seventh Day of September, 1994

Attest:

BRUCE LEHMAN

*Attesting Officer*     *Commissioner of Patents and Trademarks*